United States Patent
Mihalik

(10) Patent No.: US 6,787,568 B1
(45) Date of Patent: Sep. 7, 2004

(54) ANTIBIOTIC/ANALGESIC FORMULATION AND A METHOD OF MAKING THIS FORMULATION

(75) Inventor: Richard Mihalik, St. Joseph, MO (US)

(73) Assignee: Phoenix Scientific, Inc., St. Joseph, MO (US)

( * ) Notice: Subject to any disclaimer, the term of this patent is extended or adjusted under 35 U.S.C. 154(b) by 199 days.

(21) Appl. No.: 09/723,064

(22) Filed: Nov. 27, 2000

(51) Int. Cl.$^7$ .............................................. A61K 31/70
(52) U.S. Cl. ..................................................... 514/618
(58) Field of Search ........................................ 514/618

(56) References Cited

U.S. PATENT DOCUMENTS

| | | | | |
|---|---|---|---|---|
| 5,151,270 A | * | 9/1992 | Grimberg | 424/401 |
| 5,843,980 A | * | 12/1998 | Hall et al. | 514/438 |

FOREIGN PATENT DOCUMENTS

| WO | WO 98/50045 | * | 11/1998 |
|---|---|---|---|

OTHER PUBLICATIONS

Plumb, Donald C., Veterinary Drug Handbook, Third Edition, pp. 222–224; p. 336; pp. 355–357; pp. 371–372; pp. 587–591; and p. 1305 (1999).

Veterinary Pharmaceuticals and Biologicals, 1999/2000, pp. 557–558, Edition 11, Veterinary Medicine Publishing Group, Lenexa, KS, copyright 1998.

Compendium of Veterinary Products, Product Labels/Monographs, Jun. 2003, USA Edition, Nuflor® Injectable Solution 300 mg/ml.

\* cited by examiner

*Primary Examiner*—Elli Peselev
(74) *Attorney, Agent, or Firm*—Susan J. Wharton; Stinson Morrison Hecker LLP

(57) ABSTRACT

A formulation that includes a mixture of at least one antibiotic, at least one analgesic, and at least one solvent is provided. The antibiotic and the analgesic are dissolved in the solvent to form a formulation that is suitable for veterinary applications. This formulation can be administered to animals as a pour-on or an injectable formulation.

17 Claims, No Drawings

ANTIBIOTIC/ANALGESIC FORMULATION AND A METHOD OF MAKING THIS FORMULATION

STATEMENT REGARDING FEDERALLY SPONSORED RESEARCH OR DEVELOPMENT

Not Applicable.

CROSS-REFERENCE TO RELATED APPLICATIONS

Not Applicable.

BACKGROUND OF THE INVENTION

The present invention relates to a formulation for fighting infection, counteracting inflamation, and reducing fever. More specifically, the present invention relates to an antibiotic/analgesic formulation for use in veterinary applications.

Antibiotics and analgesics are currently available in separate formulations, but they are frequently administered at about the same time. One disadvantage with formulations currently available is that antibiotics and analgesics must be administered separately. As a result, two dosages must be administered each time both are administered.

In order to overcome this disadvantage, formulations that include both an antibiotic and an analgesic are needed. These formulations should be usable in pour-on or injectable forms.

SUMMARY OF THE INVENTION

It is an object of the present invention to provide a formulation that contains both an antibiotic and an analgesic so that both can be administered together.

It is a further object of the present invention to provide a method of making an antibiotic/analgesic formulation.

According to the present invention, the foregoing and other objects are achieved by a pour-on or an injectable antibiotic/analgesic formulation that includes a mixture of an antibiotic, an analgesic, and at least one solvent.

Additional objects, advantages and novel features of the invention will be set forth in part in the description which follows, and in part will become apparent to those skilled in the art upon examination of the following, or may be learned from the practice of the invention. The objects and advantages of the invention may be realized and attained by means of the instrumentalities and combinations particularly pointed out in the appended claims.

DETAILED DESCRIPTION OF THE PREFERRED EMBODIMENTS

The formulation of the present invention is an effective pour-on or injectable formulation for fighting infection, counteracting inflammation, and reducing fever. This formulation includes an antibiotic, an analgesic, and at least one solvent.

The antibiotic in the formulation of the present invention functions to suppress or destroy microorganisms and acts to treat and prevent diseases. The antibiotic that may be used in this formulation includes, but is not limited to, florfenicol, any salt of oxytetracycline including oxytetracycline dihydrate, chlortetracycline, tetracycline, gentamicin, chloramphenicol, tylosin, cephalosporins, or combinations thereof.

The analgesic in the formulation of the present invention acts as an anti-inflammatory and an antipyretic. It counteracts inflamation, reduces fever, and relieves pain. It may be in a steroidal or non-steroidal form. The analgesic that may be used in this formulation includes, but is not limited to, dexamethasone, flunixin meglumine, or combinations thereof.

The solvent that may be used in the formulation of the present invention may include, but is not limited to, N-methyl-2-pyrrolidone, glycerol formal, 2-pyrrolidone, polyethylene glycol, propylene glycol, glycerine, N,5-dimethyl-2-pyrrolidone, 3,3-dimethyl-2-pyrrolidone, N-ethyl-2-pyrrolidone, N-ethyloxy-2-pyrrolidone, N-ethylene-2-pyrrolidone, 1-pyrrolidone, water, diethylene glycol monobutyl ether, benzyl benzoate, isopropyl alcohol, xylenes, or combinations thereof. When florfenicol is used as the antibiotic, however, water should not be used as the only solvent.

While an antibiotic, analgesic, and a solvent are the only components necessary in the formulation of the present invention, a number of optional components may be added to enhance various properties of the formulation. Such optional components may include an antioxidant, a solubilizing agent, a complexing agent, a preservative, a pH adjusting agent, a buffer, or combinations thereof.

Examples of antioxidants that may be used include, but are not limited to, edetate disodium, sodium metabisulfite, sodium formaldehyde sulfoxylate, vitamin E acetate, vitamin C, vitamin $B_{12}$, or combinations thereof. Preferably, sodium formaldehydesulfoxylate is included in the formulation when any salt of oxytetracycline is part of the formulation.

The solubilizing agent for the formulation of the present invention may be, but is not limited to, cross-linked polypyrrolidone such as povidone C-15 (having 15 monomer units), magnesium oxide, calcium oxide, or combinations thereof. Preferably, a solubilizing agent is included in the formulation when any salt of oxytetracycline is part of the formulation.

Complexing agents are a type of solubilizing agent and may be present as the solubilizing agents listed above or in addition to the solubilizing agents. Examples of complexing agents that may be used include, but are not limited to, calcium oxide, calcium chloride, magnesium oxide, borate salts, any soluble polymer of 2-pyrrolidone such as cross-linked polypyrrolidone or polyvinyl pyrrolidone, or combinations thereof.

Examples of preservatives that may be used include, but are not limited to, benzyl alcohol, ethyl alcohol, parabens such as methyl-, ethyl-, propyl-, or butylparaben, chlorobutanol, sodium benzoate, benzoic acid, myristyl-gamma-picolinium chloride, benzalkonium chloride, benzethonium chloride, cetylpyridinium chloride, chlorocresol, cresol, dehydroacetic acid, methylparaben sodium, phenol, phenylethyl alcohol, potassium benzoate, potassium sorbate, propylparaben sodium, sodium dehydroacetate, sodium propionate, sorbic acid, thymol, or combinations thereof.

The pH adjusting agent may be hydrochloric acid. The buffer may be monoethanolamine.

The antibiotic desirably is present in the formulation in an amount effective to suppress or destroy unwanted microorganisms. The total amount of antibiotic used in the formulation of the present invention may be about 1–60% weight/volume (w/v). Preferably, the formulation of the present invention includes about 15–40% w/v antibiotic. Most preferably, the formulation includes about 30–40% w/v antibiotic. If oxytetracycline dihydrate is used as the antibiotic, then an antioxidant such as sodium formaldehyde sulfoxylate should be used therewith.

The analgesic desirably is present in the formulation in an amount effective to counteract inflammation and reduce fever. If flunixin meglumine is used as the analgesic, then it should be present in the formulation of the present invention in an amount of about 2–15% w/v. Preferably, if flunixin meglumine is used, the formulation has about 5–12% w/v flunixin meglumine. Most preferably, about 8–10% w/v of flunixin meglumine is used. The amount of flunixin in the flunixin meglumine should be about 1–5% w/v. Alternatively, dexamethasone may be used as the analgesic agent, and in that case, about 0.01–5% w/v is used. Preferably, about 0.03–1% dexamethasone is used, and most preferably, about 0.05–0.1% dexamethasone is used.

The amount of solvent used in the formulation of the present invention should be sufficient to dissolve all of the components of the formulation. The solvent should be present in an amount between about 20–95% w/v depending on the concentration of antibiotic and analgesic present in the formulation.

It is desirable to add a preservative to the formulation of the present invention. The preservative functions as an antibacterial or antimicrobial agent. The total amount of preservative in this formulation is about 0–15% w/v. Preferably, a preservative is present in an amount of about 0.01–10% w/v. Most preferably, a preservative is about 0.5–3% w/v of the formulation.

If an antioxidant is present in the formulation, it is about 0.005–3% w/v of the formulation. Preferably, it is about 0.1–1% w/v of the formulation.

If a cross-linked polypyrrolidone is used as a solubilizing or complexing agent in the formulation, it is present as about 1–10% w/v of the formulation. If magnesium or calcium containing components are present in the formulation, each is about 1–20% w/v of the formulation. If pyrrolidone containing components are present, they are about 5–90% w/v of the formulation, and preferably, they are about 30–50% of the formulation.

The antibiotic/analgesic formulation of the present invention may be administered as a pour-on product or as a parenteral formulation. Preferably, it is administered as a parenteral injection formulation to cats, dogs, horses, cattle, pigs, sheep, or poultry. Typically, the formulation is administered to animals in a dosage of 0.5–200 mg/kg of animal depending upon the severity of the pain, inflamation, fever and/or infection and depending upon the type of animal being treated. Preferably, it is administered in a dosage of 1–150 mg/kg. If water is used in the formulation, the pH of the formulation should be between about 4 and 10. Preferably, the formulation has a pH between about 6 and 8.

The following are examples of various antibiotic/analgesic formulations of the present invention and methods of making these formulations. These methods are within the scope of this invention. These examples are not meant in anyway to limit the scope of this invention.

EXAMPLE 1

N-methyl-2-pyrrolidone was added to a vessel. Agitation began. With continued agitation, a quantity of florfenicol amounting to 30% w/v of the final formulation was added to the solvent and mixed with the solvent until it dissolved. A quantity of flunixin meglumine amounting to 4.15% w/v of the final formulation was then added and mixed into the solution. This flunixin meglumine was 2.5% w/v flunixin. Next, benzyl alcohol was added in a quantity amounting to 2% w/v. of the final formulation, and the resulting solution was mixed until all components were adequately dissolved. With continued agitation, a supplemental amount of N-methyl-2-pyrrolidone was added in an amount sufficient to completely dissolve any remaining undissolved components. The total amount of N-methyl-2-pyrrolidone added made up the balance of the formulation. The resulting formulation can be used for parenterally or as a pour-on.

EXAMPLE 2

N-methyl-2-pyrrolidone was added to a vessel. Agitation began. With continued agitation, a quantity of florfenicol amounting to 60% w/v of the final formulation was added to the solvent and mixed with the solvent until it dissolved. A quantity of flunixin meglumine amounting to 8.29% w/v of the final formulation was then added and mixed into the solution. This flunixin meglumine was 5.00% w/v flunixin. Next, benzyl alcohol was added in a quantity amounting to 2% w/v of the final formulation, and the resulting solution was mixed until all components were adequately dissolved. With continued agitation, a supplemental amount of N-methyl-2-pyrrolidone was added in an amount sufficient to completely dissolve any remaining undissolved components. The total amount of N-methyl-2-pyrrolidone added made up the balance of the formulation. The resulting formulation can be used parenterally.

EXAMPLE 3

N-methyl-2-pyrrolidone was added to a vessel. Agitation began. With continued agitation, a quantity of florfenicol amounting to 60% w/v of the final formulation was added to the solvent and mixed with the solvent until it dissolved. A quantity of flunixin meglumine amounting to 8.29% w/v of the final formulation was then added and mixed into the solution. This flunixin meglumine was 5.00% w/v flunixin. Next, benzyl alcohol was added in a quantity amounting to 10% w/v of the final formulation, and the resulting solution was mixed until all components were adequately dissolved. With continued agitation, a supplemental amount of N-methyl-2-pyrrolidone was added in an amount sufficient to completely dissolve any remaining undissolved components. The total amount of N-methyl-2-pyrrolidone added made up the balance of the formulation. The resulting formulation can be used parenterally.

EXAMPLE 4

N-methyl-2-pyrrolidone was added to a vessel. Agitation began. With continued agitation, a quantity of florfenicol amounting to 50% w/v of the final formulation was added to the solvent and mixed with the solvent until it dissolved. A quantity of flunixin meglumine amounting to 6.91% w/v of the final formulation was then added and mixed into the solution. This flunixin meglumine was 4.17% w/v flunixin. Next, benzyl alcohol was added in a quantity amounting to 8.33% w/v of the final formulation, and the resulting solution was mixed until all components were adequately dissolved. With continued agitation, glycerol formal amounting to 16.6% w/v of the final formulation was added to the solution. With continued agitation, a supplemental amount of N-methyl-2-pyrrolidone was added in an amount sufficient to completely dissolve any remaining undissolved components. The total amount of N-methyl-2-pyrrolidone added made up the balance of the formulation. The resulting formulation can be used parenterally.

EXAMPLE 5

Water was added to a vessel. Agitation began. With continued agitation, a quantity of flunixin meglumine amounting to 2.77% w/v of the final formulation was added to the water and mixed with the water until it dissolved. This flunixin meglumine was 1.67% w/v flunixin. Next, 2-pyrrolidone was added in a quantity amounting to 40% w/v of the final formulation. Povidone C-15 cross-linked polypyrrolidone (having 15 monomer units) was then added in a quantity amounting to 5.00% w/v of a final formulation. Following this, magnesium oxide was added in a quantity amounting to 1.80% w/v of the final formulation. Sodium formaldehyde sulfoxylate was then added in a quantity amounting to 0.20% w/v of the final formulation. Next, monoethanolamine was added in a quantity amounting to 0.3% w/v of the final formulation. A quantity of oxytetracycline dihydrate amounting to 24.04% w/v of the final formulation was then added and mixed into the solution. This oxytetracycline dihydrate was 20.0% w/v oxytetracycline. The pH of the formulation was adjusted by adding hydrochloric acid in the amount of 0.022% w/v of the final formulation, and the resulting solution was mixed until all components were adequately dissolved. With continued agitation, a supplemental amount of water was added in an amount sufficient to completely dissolve any remaining undissolved components. The total amount of water added made up the balance of the formulation. The resulting formulation can be used parenterally.

EXAMPLE 6

Water was added to a vessel. Agitation began. With continued agitation, a quantity of gentamicin base as gentamicin sulfate amounting to 8.50% w/v of the final formulation was added to the water and mixed with the water until it dissolved. A quantity of dexamethasone amounting to 0.03% w/v of the final formulation was then added and mixed into the solution. Next, polyethylene glycol 400 (having an average molecular weight of 400 as defined in The Merck Index, 12th edition, 1996) was added to the formulation in a quantity amounting to 7.5% w/v of the final formulation. Next, ram sodium metabisulfite was added in a quantity amounting to 0.272% w/v of the final formulation. Following this, benzyl alcohol was added in a quantity amounting to 0.135% w/v of the final formulation. Next, methylparaben was added in a quantity amounting to 0.180% w/v of the final formulation, and then propylparaben was added in a quantity amounting to 0.020% w/v of the final formulation. Ethyl alcohol (95%) was then added in a quantity amounting to 0.75% w/v of the final formulation. Next, edetate disodium was added in a quantity amounting to 0.0085% w/v of the final formulation, and the resulting solution was mixed until all components were adequately dissolved. With continued agitation, a supplemental amount of water was added in amount sufficient to completely dissolve any remaining undissolved components. The total amount of water added made up the balance of the formulation. The resulting formulation can be used parenterally.

EXAMPLE 7

N-methyl-2-pyrrolidone was added to a vessel. Agitation began. With continued agitation, a quantity of florfenicol amounting to 30% w/v of the final formulation was added to the solvent and mixed with the solvent until it dissolved. A quantity of dexamethasone amounting to 0.067% w/v of the final formulation was then added and mixed into the solution. Benzyl alcohol amounting to 2.3% w/v of the final formulation was then added to the solution. Next, polyethylene glycol 400 was added in a quantity amounting to 16.75% w/v of the final formulation. Methylparaben amounting to 0.0603% w/v of the final formulation and propylparaben amounting to 0.0067% w/v of the final formulation were then added to the solution. Following this, ethyl alcohol was added in a quantity amounting to 1.675% w/v of the final formulation. Water was then added in a quantity amounting to 14.6% w/v of the final formulation, and the resulting solution was mixed until all components were adequately dissolved. With continued agitation, a supplemental amount of N-methyl-2-pyrrolidone was added in an amount sufficient to completely dissolve any remaining undissolved components. The total amount of N-methyl-2-pyrrolidone added made up the balance of the formulation. The resulting formulation can be used parenterally or as a pour-on.

From the foregoing, it will be seen that this invention is one that is well adapted to attain all the ends and objects herein above set forth together with other advantages which are obvious and inherent to the formulation. It will be understood that certain features and subcombinations are of utility and may be employed without reference to other features and subcombinations. This is contemplated by and is within the scope of the claims. Since many possible embodiments may be made of the invention without departing from the scope thereof, it is to be understood that all matter herein set forth is to be interpreted as illustrative and not in a limiting sense.

I claim:

1. An analgesic/antibiotic formulation for veterinary use, comprising a mixture of:
   - at least one antibiotic selected from the group consisting of florfenicol, chloramphenicol, and combinations thereof;
   - at least one analgesic; and
   - at least one solvent, wherein said antibiotic and said analgesic are dissolved in said solvent to form a mixture that is a systemic formulation.

2. The formulation of claim 1, wherein said analgesic is selected from the group consisting of flunixin meglumine, dexamethasone, and combinations thereof.

3. The formulation of claim 1, wherein said solvent is selected from the group consisting of N-methyl-2-pyrrolidone, 2-pyrrolidone, N-5-dimethyl-2-pyrrolidone, 3-3-dimethyl-2-pyrrolidone, N-ethyl-2-pyrrolidone, N-ethyloxy-2-pyrrolidone, N-ethylene-2-pyrrolidone, 1-pyrrolidone, glycerol formal, propylene glycol, polyethylene glycol, glycerine, water, diethylene glycol monobutyl ether, benzyl benzoate, isopropyl alcohol, xylenes, and combinations thereof.

4. The formulation of claim 1, further comprising:
   a preservative.

5. The formulation of claim 4, wherein said preservative is selected from the group consisting of benzyl alcohol, ethyl alcohol, parabens, chlorobutanol, sodium benzoate, benzoic acid, myristyl-gamma-picolinium chloride, benzalkonium chloride, benzethonium chloride, cetylpyridinium chloride, chlorocresol, cresol, dehydroacetic acid, methylparaben sodium, phenol, phenylethyl alcohol, potassium benzoate, potassium sorbate, propylparaben sodium, sodium dehydroacetate, sodium propionate, sorbic acid, thymol, and combinations thereof.

6. The formulation of claim 1, further comprising:
   one or more components selected from the group consisting of an antioxidant, a solubilizing agent, a buffer, and a complexing agent.

7. The formulation of claim 6, wherein said formulation is comprised of an antioxidant selected from the group consisting of edetate disodium, sodium metabisulfite, sodium formaldehyde sulfoxylate, vitamin E acetate, vitamin C, vitamin B12, and combinations thereof.

8. The formulation of claim 7, wherein said antioxidant is sodium formaldehyde sulfoxylate.

9. The formulation of claim 1, wherein said formulation is comprised of about 5–60% w/v antibiotic, about 0.01–15% w/v analgesic, and about 20–95% w/v solvent.

10. The formulation of claim 1, wherein said formulation is comprised of about 15–40% w/v antibiotic, about 0.03–12% analgesic, and about 20–85% w/v solvent.

11. The formulation of claim 1, wherein said formulation has a pH between about 4 and 10.

12. A method of making an antibiotic/analgesic formulation, comprising:

mixing an antibiotic selected from the group consisting of florfenicol, chloramphenicol, and combinations thereof with a solvent to form a solution;

adding an analgesic to said solution; and mixing said solution to form a systemic antibiotic/analgesic formulation.

13. The method of claim 12, further comprising:

adding to said formulation one or more components selected from the group consisting of a preservative, an antioxidant, a complexing agent, a pH adjusting agent, a buffer, and a solubilizing agent.

14. A method for treating infection, counteracting inflammation and reducing fever in an animal, comprising:

administering to an animal in need thereof a systemic formulation comprising a mixture of an antibiotic selected from the group consisting of florfenicol, chloramphenicol, and combinations thereof, an analgesic, and a solvent.

15. The method of claim 14, wherein said formulation is a parenterally injectable formulation and is injected through the skin of said animal.

16. The method of claim 15, wherein said animal is a cat, dog, horse, cow, pig, sheep, or poultry.

17. The method of claim 15, wherein said formulation is administered in a dosage of about 0.5–200 mg/kg of animal.

* * * * *